United States Patent [19]

Lu et al.

[11] Patent Number: 4,716,233

[45] Date of Patent: Dec. 29, 1987

[54] PROCESS FOR PREPARING PHTHALIMIDO ISOXAZOLES

[75] Inventors: Jing-Jong Lu; Herbert L. Wehrmeister, both of Terre Haute, Ind.

[73] Assignee: International Minerals & Chemical Corp., Terre Haute, Ind.

[21] Appl. No.: 834,686

[22] Filed: Feb. 28, 1986

Related U.S. Application Data

[62] Division of Ser. No. 765,964, Aug. 15, 1985, Pat. No. 4,593,024.

[51] Int. Cl.$^4$ ........................................... C07D 261/04
[52] U.S. Cl. .................................................. 548/245
[58] Field of Search ........................................ 548/245

[56] References Cited

U.S. PATENT DOCUMENTS 4,322,429  3/1982  Burrow, Jr. ...................... 548/245

OTHER PUBLICATIONS

Nefkens, *Nature*, vol. 185, p. 309, (1960).
Baldwin, *J. Amer. Chem. Soc.*, vol. 103, pp. 942–943, (1981).

*Primary Examiner*—Robert W. Ramsuer
*Attorney, Agent, or Firm*—W. R. Guffey; T. L. Farquer

[57] ABSTRACT

Novel dihydroisoxazole compounds are disclosed having activity against parasitic worms and showing little or no toxicity to the host animal. These compounds are 3-chloro-4-dialkylaminophthaloylamino-4,5-dihydroisoxazoles and 3-dialkylamino-4-dialkylaminophthaloylamino-4,5-dihydroisoxazoles. A process for making these compounds and a method of administering them to infested animals is also disclosed.

1 Claim, No Drawings

PROCESS FOR PREPARING PHTHALIMIDO ISOXAZOLES

This is a division of application Ser. No. 765,964, filed Aug. 15, 1985, now U.S. Pat. No. 4,593,024.

BACKGROUND OF THE INVENTION

Parasitic worms afflict mammals and fowl and thus pose an economic problem in the raising of cattle, swine, poultry and fur-bearing mammals. A signicant number of compounds containing an amidine structural feature have shown significant anthelmintic activity, e.g., levamisole, albendazole, thiabendazole, morantel and bunamidine. However, a compound that is active against one type of worm is not necessarily active against other types. Likewise, toxicity often varies from one host animal to the next. Therefore there is a need for new agents with activities against a broad spectrum of endoparasitic worms and with low toxicity toward the host.

Numerous isoxazoles, isoxazolines and isoxazolidines have been isolated from natural sources or synthesized, and individual compounds or closely-related groups of compounds have been reported to be active as herbicides, anti-protozoan drugs, hypoglycemic agents, anti-inflammatory agents, or anti-pyretic agents. It is obvious that having activity against one particular pest or biological dysfunction does not mean a compound will also be active against parasitic worms. In addition, the activity of a compound even against a single pest is almost impossible to predict from its structure. For example, two structurally similar compounds can have dramatically different anthelmintic activities, one being very effective and the other totally ineffective.

SUMMARY OF THE INVENTION

It is an object of the invention to provide new compounds having anthelmintic activity.

It is an additional object of the present invention to provide new compounds having activity against gastrointestinal nematode infestations and cestode infestations in animals with low toxicity toward the host.

It is another object of this invention to provide a method of treating mammals or fowl which are infested with parasitic worms or treating mammals or fowl to prevent infestation by parasitic worms.

It is a further object of the invention to provide a process for synthesizing the new compounds.

In accordance with this invention there are provided anthelmintic compounds of the formula:

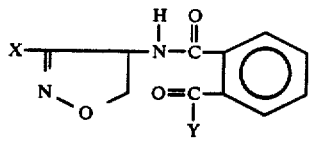

wherein X is chlorine or a dialkylamino group and Y is a dialkylamino group, when X is a dialkylamino group it is the same group as Y, said dialkylamino group being selected from the group consisting of diethylamino, morpholino, pyrrolidino and 4-methylpiperazino.

The invention also contemplates a particularly useful method of preparing 3-chloro-4-phthalimido-4,5-dihydroisoxazole, an intermediate for the preparation of the claimed and other compounds. Other embodiments of this invention provide a method for making the claimed compounds and a method of treating mammals or fowl prophylactically or therapeutically after infestation with parasitic worms.

When used at an effective dosage, the compounds of the present invention cause little or no toxicity to the hot animals. This provides an obvious benefit in the husbandry of these animals.

DETAILED DESCRIPTION OF THE INVENTION

The isoxazoles of this invention have the formula

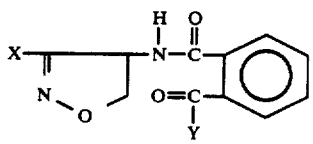

wherein X is chlorine or a dialkylamino group and Y is a dialkylamino group, said dialkylamino group being selected from the group consisting of diethylamino, morpholino, pyrrolidino and 4-methylpiperazino. Highest activity appears in those compounds where X is chlorine. When X is a dialkylamino group, it is the same group as Y.

The compounds of the invention effectively control nematode endoparasites without harm to the host animal when used at an effective dosage. Each of the compounds of this invention are effective to control the pinworm *A. tetraptera*. The most active compound against the pinworm *A. tetraptera* results when X is chlorine and Y is a morpholino group. This particular compound, 3-chloro-4-morpholinophthaloylamino-4,5-dihydroisoxazole, also shows activity againt the tapeworm *H. nana*.

Preparation of the compounds of this invention from D-cycloserine can be achieved by first protecting the active amino group by reacting D-cycloserine with a phthaloyl-containing compound to form a phthalimide with the 4-amino group of the D-cycloserine. One appropriate means is the use of N-carboethoxyphthalimide as the phthaloyl-containing compound as reported by Nefkens (Nature 185, 309, 1960). This reaction can be carried out in the presence of sodium carbonate in aqueous solution at room temperature. Alternative methods of protecting the active amino group include using O-methoxy-carbonylbenzoyl chloride as the phthaloyl-containing compound instead of N-carboethoxyphthalimide, as described by Hoogwater (Recueil de Travaux Chimiques de Pays-Bas, 92, 819–825, 1973), and via silylation followed by reaction with phthaloyl chloride as described by Kume (Tetrahedron Letters, 23, 4365, 1982).

After the amino group has been protected, the ring system is modified by reaction with a phosphorous chloride. For example, the correspondng imidoyl chloride, 3-chloro-4-phthalimido-4,5-dihydroisoxazole, can be formed by reaction with phosphorous oxychloride, as described in (J. Amer. Chem. Soc. 103, 942 (1981). Alternative methods of forming the imidoyl chloride include reaction with phosphorous pentachloride in refluxing nitromethane. This, however, is a harsher method and tends to result in a lower yield of desired product and the formation of the undesired by-product 3-(3-keto-4-phthalimido-isoxazolidin-2-yl)-4-phthalimido-4,5-dihydroisoxazole.

The imidoyl chloride, 3-chloro-4-phthalimido-4,5-dihydroisoxazole, is a useful intermdiate which can be used to make the compounds of this invention, as well as other compounds.

To form the compounds of the present invention, dialkylamines are added to the phthaloyl group by reacting the 3-chloro-4-phthalimido-4,5-dihydroisoxazole with a dialkylamine selected from the group consisting of: diethylamine, morpholine, pyrrolidine, and methylpiperazine. This reaction is carried out in a suitable solvent such as tetrahydrofuran. This results in the most active class of products: 3-chloro-4-dialkylaminophthaloylamino-4,5-dihydroisoxazoles. If the chlorine atom is then substituted by the dialkylamine, in a nucleophilic reaction which occurs at higher temperatures or after longer reaction times, other products of this invention result: 3-dialkylamino-4-dialkylaminophthaloylamino-4,5-dihydroisoxazoles.

Reaction conditions favoring substitution of the chlorine atom are typically temperatures from about 40° C. to about 80° C., preferably about 60° C., and times from about 18 to about 48 hours. Reaction conditions which do not favor the substitution of the chlorine atom are typically temperatures from about 0° C. to about 20° C. and times from about 2 hours to about 24 hours.

The products of the invention can be isolated by first concentrating the reaction mixture, for example in an evaporator, and then recrystallizing the compounds from the residue in a suitable solvent, such as ethyl acetate, or purifying by flash chromatography on silica gel and eluting with an appropriate solvent system, such as petroleum ether, ethyl acetate, methanol or mixtures thereof. Other methods of purification will be apparent to those skilled in the art.

Parasitic worms afflict both mammals and birds, therefore the present invention is useful in the raising and husbandry of livestock such as cattle, swine, sheep and goats, domestic pets such as dogs and cats, rabbits, poultry such as chickens, turkeys, ducks and geese, and fur-bearing animals such as mink, foxes and chinchilla. The compounds of the present invention can be administered orally by conventional means and techniques known in the art. They can be used prophylactically to protect animals or therapeutically after the animals have been infested.

In general, prophylactic dosages will be lower than those for pre-existing infestations. For example, dosages as low as 1 mg/kg of body weight administered regularly may be sufficient to protect an animal from infestation by parasitic worms. Therapeutic dosages will often be from 10 to 100 times greater than prophylactic dosages.

The dosage used will depend on: (1) the animal to be treated; (2) which compound is to be used; and (3) the time and method of administration. Determination of the proper dosage in light of these variables is within the control and competence of one skilled in the art.

The chemotherapeutic agents of this invention can be administered in any of a variety of forms, alone or in combination, with other pharmaceuticals. They can be administered in a solid form or in liquid form in a suitable solvent. For example, they may be administered orally in admixture with an animal feed or fed separately as a supplement. Appropriate amounts of anthelmintic compound for therapeutic treatment of pre-existing infestations are often from about 300 ppm to about 2000 ppm of animal feed.

Suitable therapeutic dosages are often from about 0.5 to about 200 mg of active ingredient per kg of body weight of the host animal, depending on the agent, the infesting pest, the degree of infestation and the program of administering.

EXAMPLE 1

Phthaloylation of D-cycloserine with N-carboethoxyphthalimide

D-cycloserine (15.3 g, 0.15 moles) and sodium carbonate (15.9 g, 0.15 mole) were dissolved in 200 ml of water. N-carboethoxyphthalimide (36.0 g, 0.164 mole) was added to the solution and the mixture was stirred for 25 minutes and filtered to remove unreacted N-carboethoxyphthalimide (12.1 g). The filtrate was chilled on ice and acidified with 4N HCl. Phthaloyl-D-cycloserine (18.5 g) precipitated out of solution and was collected by filtration, air dried, and recrystallized from ethyl acetate.

EXAMPLE 2

The synthesis of 3-chloro-4-phthalimido-4,5-dihydroisoxazoline

The compound prepared in Example 1, phthaloyl-D-cycloserine (9.28 g, 40 mmole), was dissolved in 100 ml of nitromethane. Phosphorous oxychloride (4 ml, 43 mmole) was added to the solution, which was then heated up to 100° C. in a two-hour period and kept at that temperature for an additional hour. The mixture was cooled to room temperature, and the solids were filtered off. The filtrate was concentrated, and the residue was extracted with ethyl acetate. The solvent was removed and the product was purified by flash chromatography and eluted with 3:1 petroleum ether/ethyl acetate to yield 3-chloro-4-phthalimido-4,5-dihydroisoxazole (5.49 g).

EXAMPLE 3

The preparation of 3-chloro-4-diethylaminophthaloylamino-4,5-dihydroisoxazoline

3-Chloro-4-phthalimido-4,5-dihydroisoxazole (1.0 g, 4 mmole) was dissolved in 25 ml of dried tetrahydrofuran and cooled to 0° C. Diethylamine (25 ml) was added to the solution which was then stirred at room temperature for 24 hours. The product was concentrated and the residue purified by flash chromatography and eluted with 1:1 petroleum ether-ethyl acetate. The yield was 48.6%.

EXAMPLE 4

The preparation of 3-chloro-4-morpholinophthaloylamino-4,5-dihydroisoxazole

3-Chloro-4-phthalimido-4,5-dihydroisoxazole (6 g, 24 mmole) was dissolved in 200 ml of dried tetrahydrofuran, after which morpholine (20.9 g, 240 mmole) was added. The reaction solution was heated to 60° C. and kept at this temperature for 4 hours. The resulting solution was concentrated and the residue was purified by flash chromatography and eluted with 1:1, 1:2 petroleum ether-ethyl acetate, ethyl acetate. Yield was 46.9%.

EXAMPLE 5

The preparation of 3-chloro-4-pyrrolidinophthaloylamino-4,5-dihydroisoxazole

3-Chloro-4-phthalimido-4,5-dihydroisoxazole (7.5 g, 30 mmole) was dissolved in 200 ml of dried tetrahydrofuran and cooled to 0° C. Pyrrolidine (10.67 g, 150 mmole) was added and the solution stirred for 2 hours on ice. The resulting solution was concentrated at room temperature to remove solvent and excess pyrrolidine. The residue was purified by flash chromatography on silica gel and eluted with ethyl acetate, 5:1 ethyl acetate-methanol. Yield was 78.6%.

EXAMPLE 6

The preparation of 3-morpholino-4-morpholino-phthaloylamino-4,5-dihydroisoxazole 3-Chloro-4-phthalimido-4,5-dihydroisoxazole (10 g, 40 mmole) was dissolved in 50 ml of dried tetrahydrofuran. Morpholine (34.85 g, 400 mmole) was added to the solution at room temperature. The reaction solution was heated at 60° C. for 18 hours. The product was concentrated and the residue purified by flash chromatography and eluted with 1:1, 1:2 petroleum ether-ethyl acetate, ethyl acetate, 5:1 ethyl acetate-methanol. Yield of the desired product was 92.3%.

EXAMPLE 7

The preparation of 3-(4-methylpiperazino)-4-(4-methylpiperazinophthaloylamino)-4,5-dihydroisoxazole 3-Chloro-4-phthalimido-4,5-dihydroisoxazole (5 g, 20 mmole) was dissolved in 50 ml of dried tetrahydrofuran. N-methylpiperazine (20.0 g, 200 mmole) was added to the solution at room temperature, after which the solution was heated at 60° C. for 24 hours. The solution was cooled to room temperature and the precipitated material was removed by filtration. The filtrate was concentrated and the residue was purified by flash chromatography on activated, neutral aluminium oxide and eluted with ethyl acetate, 5:1 ethyl acetate-methanol. Yield of the desired product was 49.4% with 23.8% by-product containing only one methylpiperazino group.

EXAMPLE 8

The preparation of 3-pyrrolidino-4-pyrrolidinophthaloylamino-4,5-dihydroisoxazole 3-Chloro-4-pyrrolidinophthaloylamino-4,5-dihydroisoxazole (5.34 g, 16.6 mmole) was dissolved in 100 ml of dried tetrahydrofuran. Pyrrolidine (10 ml) was added to the solution at room temperature. The reaction solution was stirred for two days at room temperature. The resulting solution was concentrated and purified by flash chromatography on silica gel and eluted with ethyl acetate, 5:1 ethyl acetate-methanol. Yield of the product compound was 5.89 g (99.5%).

EXAMPLE 9

The compounds described above were administered to worm-infested mice in their diet at 1000 ppm of feed, and the reductions in worm number were recorded. The anthelmintic activity is based on reduction in worm burden and expressed as percent effectiveness. These compounds demonstrate no toxicity in mice when fed at levels of about 100 mg/kg of body weight. The results are tabulated below:

| Phthaloylamino-4,5-dihydroisoxazole | Percent Effectiveness Against | |
|---|---|---|
| | A. tetraptera | H. nana |
| 3-Chloro-4-diethylamino | 86 | 0 |
| 3-Chloro-4-morpholino | 100 | 36 |
| 3-Chloro-4-pyrrolidino | 77 | 0 |
| 3-Morpholino-4-morpholino | 62 | 0 |
| 3-(4-Methylpiperazino-4-(4-methylpiperazino) | 42 | 0 |
| 3-Pyrrolidino-4-pyrrolidino | 40 | 0 |

What is claimed is:

1. The process of making 3-chloro-4-phthalimido-4,5-dihydroisoxazole, which comprises reacting a phthaloyl-containing compound with D-cycloserine to form a phthalimide with the 4-amino group of the D-cycloserine and reacting said phthalimide compound with a phosphorous chloride to form the imidoyl chloride, 3-chloro-4-phthalimido-4,5-dihydroisoxazole.

* * * * *

UNITED STATES PATENT AND TRADEMARK OFFICE
CERTIFICATE OF CORRECTION

PATENT NO. : 4,716,233
DATED : December 29, 1987
INVENTOR(S) : Jing-Jong Lu et al.

It is certified that error appears in the above-identified patent and that said Letters Patent are hereby corrected as shown below:

Column 1, line 11, "signicant" should read -- significant --
Column 2, line 6, "hot" should read -- host --

Signed and Sealed this

Fourteenth Day of June, 1988

Attest:

DONALD J. QUIGG

*Attesting Officer*    *Commissioner of Patents and Trademarks*